(12) United States Patent
Treganowan et al.

(10) Patent No.: US 9,902,692 B2
(45) Date of Patent: Feb. 27, 2018

(54) PROCESS FOR ISOLATING A CAROTENOID FROM A CAROTENOID-PRODUCING BIOORGANISM

(71) Applicant: DSM IP ASSETS B.V., Heerlen (NL)

(72) Inventors: James Treganowan, Kaiseraugst (CH); Carlos Santos, Kaiseraugst (CH); Julia Kessler, Kaiseraugst (CH); Daniel Grenfell-Lee, Kaiseraugst (CH); Claudia Toniato, Kaiseraugst (CH); Christian Schaefer, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 15/300,033

(22) PCT Filed: Mar. 26, 2015

(86) PCT No.: PCT/EP2015/056594
§ 371 (c)(1),
(2) Date: Sep. 28, 2016

(87) PCT Pub. No.: WO2015/144831
PCT Pub. Date: Oct. 1, 2015

(65) Prior Publication Data
US 2017/0129854 A1 May 11, 2017

(30) Foreign Application Priority Data

Mar. 28, 2014 (EP) .................................. 14162365

(51) Int. Cl.
| C07C 67/48 | (2006.01) |
| C07C 403/24 | (2006.01) |
| C12P 23/00 | (2006.01) |
| C11B 1/10 | (2006.01) |

(52) U.S. Cl.
CPC .............. *C07C 403/24* (2013.01); *C11B 1/10* (2013.01); *C12P 23/00* (2013.01); *C07C 2101/16* (2013.01); *C07C 2601/16* (2017.05)

(58) Field of Classification Search
CPC ...... C07C 403/24; C07C 2101/16; C11B 1/10; C12P 23/00
See application file for complete search history.

(56) References Cited

U.S. PATENT DOCUMENTS

| 6,329,557 B1 | 12/2001 | Rodriguez et al. |
| 6,504,067 B1* | 1/2003 | Montoya-Olvera .... C07C 29/76 |
| | | 568/816 |
| 2007/0161826 A1* | 7/2007 | Pena .................... C07C 29/095 |
| | | 568/824 |
| 2011/0282083 A1 | 11/2011 | Reilly et al. |

FOREIGN PATENT DOCUMENTS

| CN | 1582328 | 2/2005 |
| CN | 101774955 | 7/2010 |
| CN | 103012230 | 4/2013 |
| WO | WO 01/055100 | 8/2001 |
| WO | WO 03/038064 | 5/2003 |

OTHER PUBLICATIONS

International Search Report for PCT/EP2015/0596594, dated Jun. 23, 2015, 2 pages.
CN Appln. No. 201580020739.1, First Office Action, dated Jun. 14, 2017.

* cited by examiner

*Primary Examiner* — Yevgeny Valenrod
*Assistant Examiner* — Blaine G Doletski
(74) *Attorney, Agent, or Firm* — Nixon & Vanderhye P.C.

(57) ABSTRACT

The present invention relates to an improved process for isolating a carotenoid from a carotenoid-producing bioorganism, as well as to a formulation comprising such a carotenoid, and the use of such a solid formulation in feed products (or pre-mixes).

7 Claims, No Drawings

PROCESS FOR ISOLATING A CAROTENOID FROM A CAROTENOID-PRODUCING BIOORGANISM

This application is the U.S. national phase of International Application No. PCT/EP2015/056594 filed 26 Mar. 2015, which designated the U.S. and claims priority to EP Patent Application No. 14162365.2 filed 28 Mar. 2014, the entire contents of each of which are hereby incorporated by reference.

The present invention relates to an improved process for isolating a carotenoid from a carotenoid-producing bioorganism, as well as to a formulation comprising such a carotenoid, and the use of such a solid formulation in feed products (or premixes).

Carotenoids are organic pigments ranging in color from yellow to red that are naturally produced by certain bioorganisms, including photosynthetic organisms (e.g., plants, algae, cyano-bacteria), and some fungi. Carotenoids are responsible for the orange color of carrots, as well as the pink in flamingos and salmon, and the red in lobsters and shrimp. Animals, however, cannot produce carotenoids and must receive them through their diet.

Carotenoid pigments (e.g., (β-carotene and astaxanthin) are used industrially as ingredients for food and feed stocks, both serving a nutritional function and enhancing consumer acceptability. For example, astaxanthin is widely used in salmon aquaculture to provide the pink/red pigmentation characteristic of their wild counterparts. Some carotenoids provide potential health benefits, for example as vitamin A precursors or antioxidants (see, for example, Jyonouchi et al., Nutr, Cancer 16:93, 1991; Giovannucci et al., /. Natl. Cancer Inst. 87:1767, 1995; Miki, Pure Appl. Chem 63:141, 1991; Chew et al., Anticancer Res. 19:1849, 1999; Wang et al., Antimicrob. Agents Chemother. 44:2452, 2000). Some carotenoids such as astaxanthin, β-carotene, lycopene, lutein and zeaxanthin are currently sold as nutritional supplements.

Natural carotenoids can either be obtained by extraction of plant material or by microbial synthesis; but, only a few plants are widely used for commercial carotenoid production and the productivity of carotenoid synthesis in these plants is relatively low. Microbial production of carotenoids is a more attractive production route. Examples of carotenoid-producing microorganisms (=bioorganism) include: algae (*Haematococcus pluvialis*, sold under the tradename NatuRose(™) by Cyanotech Corp., Kailua-Kona, Hi.; *Dunaliella* sp.; *Thraustochytrium* sp.), yeast (Phaffia rhodozyma, recently renamed as *Xanthophyllomyces dendrorhous; Labyrinthula* sp.; *Saccharomyces cerevisiae* and *yarrowia lipolytica*), and bacteria (*Paracoccus marcusii, Brady-rhizobium, Rhodobacter* sp., *Brevibacterium, Escherichia coli* and *Methylomonas* sp.). Additionally, recombinant production of carotenoids is also possible, since the genes involved in carotenoid biosynthesis are well-known and have been heterologously expressed in a variety of host cells (e.g., *E. coli, Candida utilis, Saccharomyces cerevisiae, Methylomonas* sp.). Thus far, few of these demonstrations are suitable to produce a carotenoid product in significant quantities in a cost-effective manner for industrial use.

The present invention relates to an improved process for isolating a carotenoid from a carotenoid-producing bioorganism, as well as to a formulation comprising such a carotenoid, and the use of such a solid formulation in feed products (or premixes).

Usually these bioorganisms produce carotenoid(s), retinolic compound(s) or other small molecule lipophilic agent(s) and accumulate the produced compound to greater than or equal to 1% of its dry cell weight.

Presently, the carotenoid is obtained as follows:

After the bioorganism has finished the production of the carotenoid, the carotenoid is isolated, washed and then further formulated into the desired application form.

Surprisingly we have found out that when the isolated carotenoid is treated at least one time with a washing step using an aqueous solution of a Brønsted acid, the carotenoid, which is obtained, has better properties (such as purity of the crystal form, which results in better formulation (stable emulsions) because of less undesired lipophilic residue from the process).

Therefore the present invention relates to a process (P) for the isolation of a carotenoid from a carotenoid-producing bioorganism comprising the following steps
(i) extraction of the carotenoid from the biomass by at least one solvent (I), and
(ii) optionally at least one washing step using at least one solvent (II), which is not miscible with the solvent (I), and
(iii) optionally drying the obtained solution which comprises the carotenoid,
characterised in that after the step (i) at least one washing step using an aqueous solution of a Brønsted acid is carried out (step (i')).

Preferred is a process wherein the Brønsted acid is chosen from the group consisting of phosphoric acid and organic acids.

More preferred the Brønsted acid is an organic acid.

More preferably the Brønsted acid is chosen from the group consisting of citric acid, tartaric acid and maleic acid.

Therefore the present invention relates to a process ($P_1$) which is process (P), wherein the Brønsted acid is chosen from the groups consisting of phosphoric acid and an organic acid.

Therefore the present invention relates to a process ($P_2$) which is process (P), wherein the Brønsted acid is an organic acid.

Therefore the present invention relates to a process ($P_3$) which is process (P), wherein the Brønsted acid is chosen from the groups consisting of citric acid, tartaric acid and maleic acid.

The concentration of the aqueous solution of the Brønsted acid in the process according to the present invention can vary. The concentration of the aqueous solution of the Brønsted acid is usually up to 10 weight-% (wt-%), based on the total weight of the aqueous solution. Usually the concentration of the Brønsted acid is at least 0.01 wt-%, preferably the concentration of the Brønsted acid is 0.01-10 wt-%, more preferred 1-5 wt-%, based on the total weight of the aqueous solution.

Therefore the present invention related to a process ($P_4$) which is process (P), ($P_1$), ($P_2$) or ($P_3$), wherein the concentration of the aqueous solution of the Brønsted acid between 0.01-10 weight-% (wt-%), based on the total weight of the aqueous solution, preferably 1-5 wt-%, based on the total weight of the aqueous solution.

The process according to the present invention can be carried out batchwise as well as continuously. Such a flexibility is also a big advantage.

The obtained crystal do have better properties than those obtained by the processes according to the prior art.

The extraction (step (i)) is usually carried out at ambient temperature (20-25° C.). But the process could also be carried out at higher or lower temperature (optionally under pressure).

Preferably the process is carried out at a temperature, which is below the boiling point of the solvent which is used for the extraction.

Preferably the extraction of the carotenoid from the biomass is carried out in at least one solvent (step (i)). This solvent or mixture of solvents is preferably water immiscible.

Suitable solvents for step (i) are for example $CH_2Cl_2$, chloroform, n-heptane and n-hexan.

Therefore the present invention relates to a process ($P_5$) which is process (P), ($P_1$), ($P_2$), ($P_3$) or ($P_4$), wherein the extraction of the carotenoid from the biomass is carried out in at least one solvent (step (i)), which is water immiscible.

Therefore the present invention relates to a process ($P_6$) which is process (P), ($P_1$), ($P_2$), ($P_3$), ($P_4$) or ($P_5$), wherein the extraction of the carotenoid from the biomass is carried out in at least one solvent (step (i)), which is chosen from the group consisting of $CH_2Cl_2$, chloroform, n-heptane and n-hexane.

The extraction (step (i)) is usually carried out at ambient temperature (20-25° C.). But the process could also be carried out at higher or lower temperature (optionally under pressure).

Preferably the process is carried out at a temperature, which is below the boiling point of the solvent which is used for the extraction (to avoid requiring the use of pressure).

The biomass can be extracted as such; or the biomass can be ground first (and optionally be dried) and then extracted; the biomass can be dried (and optionally be ground) and then extracted; or the biomass can be ground and extracted simultaneously. It is also possible to combine any of these procedures.

The process according to the present invention can also comprise one or more further washing steps. This is not an essential feature of the present invention, but in can further improve the quality of the obtained carotenoid.

Such a washing step (step (ii)) is carried out after step (i) and before and/or after step (i'). The washing step is carried out with at least one solvent (II), which is not miscible with the solvents (I) used in step (i).

Therefore the present invention relates to a process ($P_7$) which is process (P), ($P_1$), ($P_2$), ($P_3$), ($P_4$), ($P_5$) or ($P_6$), wherein one or more washing steps (step (ii)) are carried out after step (i) and before and/or after step (i').

Finally, in step (iii) the formulation can be dried to obtain the carotenoid in a dried form. But it is also possible to use the carotenoid in a solvent (or dispersed in the extraction solvent).

It also possible that after the extraction step (step (i)) to remove the solvent in an additional step. This could be useful when the whole isolation process is carried out for example at two different location and/or to store the extracted material before the next step. The transportation as well as the storage is simpler without any solvent.

The bioorganism produces carotenoid(s) (or also retinolic compound(s) or other small molecule lipophilic agent(s)) and accumulate the produced compound to greater than or equal to 1% of its dry cell weight.

The term "bioorganism", as used herein, includes, for example, animal, mammalian, insect, plant, fungal, yeast, algal, bacterial, cyanobacterial, archaebacterial and protozoal bioorganisms.

The bioorganism, which produce carotenoids, can be natural (as to be found in nature) or it can be modified.

Suitable bioorganisms are known from the prior art, i.e. from WO2006102342.

The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{200}$-$C_{30}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature.

Carotenoids include but are not limited to: antheraxanthin, adonirubin, adonixanthin, astaxanthin, canthaxanthin, capsorubrin, β-cryptoxanthin, α-carotene, β-carotene δ-carotene, ϵ-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, mimulaxanthin, neoxanthin, neurosporene, hydroxyneurosporene, peridinin, phytoene, rhodopin, rhodopin glucoside, rhodoxanthin, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-p-diglucoside, zeaxanthin, and $C_{30}$ carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester, acetylation) and sulfate derivatives (e.g., esterified xanthophylls).

Preferably the carotenoids are selected from the group consisting of astaxanthin, derivatives of astaxanthin (such as esterified astaxanthin), zeaxanthin and derivatives of zeaxanthin (such as esterified zeaxanthin).

Carotenoids produced according to the present invention can be utilized in any of a variety of applications, for example exploiting their biological or nutritional properties (e.g., anti-oxidant, etc.) and/or their pigment properties. For example, carotenoids may be used in pharmaceuticals (see, for example, Bertram, Nutr. Rev. 57:182, 1999; Singh et al., Oncology 12:1643, 1998; Rock, Pharmacol. Titer. 75:185, 1997; Edge et al, J. Photochem Photobiol 41 :189, 1997; U.S. Patent Application 2004/0116514; U.S. Patent Application 2004/0259959), food supplements (see, for example, Koyama et al, J. Photochem Photobiol 9:265, 1991 ; Bauernfeind, Carotenoids as colorants and vitamin A precursors, Academic Press, NY, 1981 ; U.S. Patent Application 2004/0115309; U.S. Patent Application 2004/0234579), electro-optic applications, animal feed additives (see, for example, Krinski, Pure Appl. Chem. 66:1003, 1994; Polazza et al., Meth. Enzymol. 213 :403, 1992), cosmetics (as anti-oxidants and/or as cosmetics, including fragrances; see for example U.S. Patent Application 2004/0127554), etc. Carotenoids produced in accordance with the present invention may also be used as intermediates in the production of other compounds (e.g., steroids, etc.).

As examples of pharmaceutical and/or health applications. astaxanthin and/or esters thereof may be useful in the treatment of inflammatory diseases, asthma, atopic dermatitis, allergies, multiple myeloma, arteriosclerosis, cardiovascular disease, liver disease, cerebrovascular disease, thrombosis, neoangiogenesis-related diseases, including cancer, rheumatism, diabetic retinopathy; macular degeneration and brain disorder, hyperlipidemia, kidney ischemia, diabetes, hypertension, tumor proliferation and metastasis; and metabolic disorders. Additionally, carotenoids and astaxanthin may be useful in the prevention and treatment of fatigue, for improving kidney function in nephropathy from inflammatory diseases, as well as prevention and treatment of other life habit-related diseases. Still further, astaxanthin has been found to play a role as inhibitors of various biological processes, including interleukin inhibitors, phosphodiesterase inhibitors, phospholipase A2 inhibitors, cyclooxygenase-2 inhibitors, matrix metalloproteinase inhibitors, capillary endothelium cell proliferation inhibitors, lipoxygenase inhibitors. See, e.g., Japanese Publication No. 2006022121, published 20060126 (JP Appl No. 2005-301156 filed 20051017); Japanese Publication No. 2006016408, published 20060119 (JP Appl No. 2005-301155 filed 20051017); Japanese Publication No. 2006016409, published 20060119 (JP Appl No. 2005-301157 filed 20051017); Japanese Publication No. 2006016407, published 20060119 (JP Appl No. 2005-301153 filed 20051017); Japanese Publication No. 2006008717, published 20060112 (JP Appl No. 2005-301151 filed 20051017); Japanese Publication No. 2006008716, published 20060112(JP Appl No. 2005-301150 filed 20051017); Japanese Publication No. 2006008720, published 20060112 (JP Appl No. 2005-301158 filed 20051017); Japanese Publication No. 2006008719, published 20060112(JP Appl No. 2005-301154 filed 20051017); Japanese Publication No. 2006008718, published 20060112(JP Appl No. 2005-301152 filed 20051017); Japanese Publication No. 2006008713, published 20060112(JP Appl No. 2005-301147 filed 20051017); Japanese Publication No. 2006008715, published 20060112 (JP Appl No. 2005-301149 filed 20051017); Japanese Publication No. 2006008714, published 20060112 (JP Appl No. 2005-301148 filed 20051017); and Japanese Publication No. 2006008712, published 20060112 (JP Appl No. 2005-301146 filed 20051017).

The carotenoids in the crystalline form as obtained by the process according to the present invention can be further formulated by methods typically applied to carotenoids.

For example, they can be used in liquid, gel-like or solid formulations. They can be formulated as emulsions/dispersion or any other commonly known form.

Therefore the present invention also relates to the use of the carotenoid obtained by the process according to the present invention as described above in the production of food products, feed products, pharmaceutical products and/or personal care products.

Furthermore the present invention also relates to the use of at least one solid formulation as described above in the production of a premix for food products, feed products, pharmaceutical products and/or for personal care products.

Furthermore the present invention also relates to food products, feed products, pharmaceutical products and/or personal care products comprising at least one solid formulation as described above.

Furthermore the present invention also relates to premixes (for food products, feed products, pharmaceutical products and/or for personal care products) comprising at least one solid formulation as described above.

The following examples serve to illustrate the invention. All parts and percentages are related to weight.

EXAMPLES

The following examples have been prepared as described in the description.

Example 1

Acetylated Astaxanthin

The biomass (*Yarrowia lipolytica*) was extracted with $CH_2Cl_2$. The so obtained solution which comprised the acetylated astaxanthin was washed with approximately double the amount of deionized water. The water phase was discarded. This washing step was repeated.

The so obtained solution was washed with an aqueous solution (3 wt-%) of citric acid.

Afterwards the citric acid solution was discarded.

The so obtained solution comprised about 1,6 wt-% (based on the total weight of the solution) of acetylated astaxanthin.

This solution was used to form an emulsion (with lignosulfonate as emulsifier). This emulsion was stable also after removal of the (organic) solvent and spray drying.

Example 2

Acetylated Astaxanthin

The biomass (*Yarrowia lipolytica*) was extracted with $CH_2Cl_2$.

This solution was divided into 3 portions and they were all washed with citric acid and after wards the solutions were combined and washed again with citric acid.

This solution was used to form an emulsion (with lignosulfonate as emulsifier). This emulsion was also stable after removal of the (organic) solvent and spray drying.

Example 3

Comparative Example

Acetylated Astaxanthin

The biomass (*Yarrowia lipolytica*) was extracted with $CH_2Cl_2$.

No citric acid washing step was carried.

The so obtained solution was intended to form an emulsion (with lignosulfonate as emulsifier).

No stable emulsion was obtained and it was not possible to use this emulsion for further formulations.

The invention claimed is:

1. A process for isolating a carotenoid from a carotenoid-producing bioorganism comprising the following steps:
   (i) extracting a carotenoid from a biomass comprising a carotenoid-producing bioorganism by bringing the biomass into contact with at least one organic solvent (I) to obtain a carotenoid-containing organic solvent solution,
   (ii) optionally conducting at least one solvent washing step of the carotenoid-containing organic solvent solution using at least one solvent (II) which is immiscible with the solvent (I) to obtain a washed carotenoid-containing organic solvent solution, and
   (iii) optionally drying the washed carotenoid-containing organic solvent solution obtained according to step (ii), wherein the process further comprises after step (i) the step of:
   (i') conducting at least one acid washing step of the carotenoid-containing organic solvent solution by contacting the carotenoid-containing organic solvent solution with an aqueous acidic solution comprising at least one Brønsted acid selected from the group consisting of citric acid, tartaric acid and maleic acid to obtain an acid-washed carotenoid-containing solution.

2. The process according to claim 1, wherein the aqueous acidic solution comprises the Brønsted acid in a concentration of between 0.5-10 wt-%, based on total weight of the aqueous acidic solution.

3. The process according to claim 1, wherein the process is carried out batchwise or continuously.

4. The process according to claim 1, wherein step (i) is carried out at a temperature below a boiling point of the solvent (I).

5. The process according to claim 1, wherein step (i) is practiced by extracting the carotenoid from the biomass with at least one water-immiscible organic solvent as the solvent (I).

6. The process according to claim 5, wherein the water-immiscible organic solvent is at least one selected from the group consisting of $CH_2Cl_2$, chloroform, n-heptane and n-hexane.

7. The process according to claim 1, wherein the at least washing step (ii) is carried out after step (i) and before and/or after step (i').

* * * * *